(12) United States Patent
Krolczyk et al.

(10) Patent No.: US 10,121,238 B2
(45) Date of Patent: Nov. 6, 2018

(54) INSPECTION METHOD AND INSPECTION LINE FOR TIRES

(71) Applicants: COMPAGNIE GENERALE DES ETABLISSEMENTS MICHELIN, Clermont-Ferrand (FR); Michelin Recherche et Technique S.A., Granges-Paccot (CH)

(72) Inventors: Cédric Krolczyk, Clermont-Ferrand (FR); Christian Leobal, Clermont-Ferrand (FR)

(73) Assignee: Compagnie Generale des Etablissements Michelin, Clermont-Ferrand (FR)

( * ) Notice: Subject to any disclaimer, the term of this patent is extended or adjusted under 35 U.S.C. 154(b) by 130 days.

(21) Appl. No.: 14/915,479

(22) PCT Filed: Sep. 24, 2014

(86) PCT No.: PCT/EP2014/070356
§ 371 (c)(1),
(2) Date: Feb. 29, 2016

(87) PCT Pub. No.: WO2015/044194
PCT Pub. Date: Apr. 2, 2015

(65) Prior Publication Data
US 2016/0225128 A1   Aug. 4, 2016

(30) Foreign Application Priority Data

Sep. 26, 2013  (FR) ..................... 13 59264

(51) Int. Cl.
*G06T 7/00* (2017.01)
*G06K 9/62* (2006.01)
(Continued)

(52) U.S. Cl.
CPC .......... *G06T 7/001* (2013.01); *G01M 17/021* (2013.01); *G01M 17/027* (2013.01);
(Continued)

(58) Field of Classification Search
CPC .. G01M 17/021; G01M 17/02; G01M 17/024; G01M 17/027; G01N 21/952;
(Continued)

(56) References Cited

U.S. PATENT DOCUMENTS 7,568,385 B2   8/2009   Maehner et al. ............... 73/146
9,288,447 B2   3/2016   Leobal et al. .......... H04N 7/18
(Continued)

FOREIGN PATENT DOCUMENTS

EP   1 959 227 A2   8/2008
EP   2 023 078 A1   2/2009
(Continued)

OTHER PUBLICATIONS

International Search Report dated Nov. 26, 2014, issued by WIPO in connection with International Application No. PCT/EP2014/070356.
(Continued)

*Primary Examiner* — Kim Vu
*Assistant Examiner* — Michael Vanchy, Jr.
(74) *Attorney, Agent, or Firm* — Fitzpatrick, Cella, Harper & Scinto

(57) ABSTRACT

A tire inspection line includes first and second inspection posts and a transfer apparatus. The first post is for macroscopic inspection and includes a driver for rotating a tire, a macro-image acquisition device for acquiring a macroscopic image of the tire, and a first processor for analyzing the macroscopic image by digital image processing, comparing the macroscopic image with a reference image, and detecting deviations in shape. The second post is for microscopic
(Continued)

inspection and includes a driver for rotating the tire, a micro-image acquisition device for acquiring a microscopic image of the tire, and a second processor for analyzing the microscopic image by digital image processing, comparing the microscopic image with a reference image representing a desired surface condition of the tire, and detecting local surface deviations. The transfer apparatus is for transferring the tire from the first post to a discharge point or to the second post.

10 Claims, 6 Drawing Sheets

(51) Int. Cl.
  *G01M 17/02* (2006.01)
  *G01N 21/952* (2006.01)
  *G01N 21/954* (2006.01)
(52) U.S. Cl.
  CPC ......... *G01N 21/952* (2013.01); *G01N 21/954* (2013.01); *G06K 9/6202* (2013.01); *G06T 2207/10056* (2013.01); *G06T 2207/30252* (2013.01)
(58) Field of Classification Search
  CPC ...... G01N 21/954; G01N 21/95; G06T 7/001; G06T 2207/10056; G06T 2207/30108; G06T 2207/30252; B29D 2030/0066; B29D 2030/546; B29D 2030/0635; B60C 25/002; B60C 25/005; B60C 25/138; B60C 25/14; B60C 25/142; B60C 11/246; G06K 9/6202
  See application file for complete search history.

(56) References Cited

U.S. PATENT DOCUMENTS

2005/0058333 A1\* 3/2005 Kaneko .................. G01B 11/24
  382/141
2006/0090557 A1\* 5/2006 Kunitake ........... B29D 30/0633
  73/146

FOREIGN PATENT DOCUMENTS

| EP | 2 172 737 A1 | 4/2010 |
|---|---|---|
| EP | 2 275 777 A1 | 1/2011 |
| JP | 2006-300678 A | 11/2006 |
| JP | 2011-226971 A | 11/2011 |
| WO | WO 2011/113711 A1 | 9/2011 |

OTHER PUBLICATIONS

J. Charlat, U.S. Appl. No. 15/024,597, filed Sep. 24, 2014.
J. Charlat, U.S. Appl. No. 15/024,614, filed Sep. 24, 2014.

\* cited by examiner

INSPECTION METHOD AND INSPECTION LINE FOR TIRES

FIELD OF THE INVENTION

The present invention relates to the field of visual monitoring of tires.

BACKGROUND

Visual inspection is widely developed in the tire manufacturing process, and is still usually based on the skill of operators responsible for verifying the absence of visible imperfections on the surfaces of tires to ensure their conformity.

To assist the operators in their search for any surface anomalies, there is a known way of using automatic inspection machines comprising drive means for rotating the tires and means for acquiring digital images, the acquired digital images then being compared with reference images. Examples of these machines are described in patents EP 1 959 227, EP 2 023 078, EP 2 172 737 and WO2011/113711.

However, the visual selection of tires that can be inspected by these automatic inspection machines is carried out by an operator. Consequently there is a risk that the operator may downgrade tires even though they are acceptable, and a risk that the operation of the inspection machines may be disrupted if the operator selects a tire that should not be accepted.

BRIEF DESCRIPTION OF THE INVENTION

The object of the present invention is to improve the process of automatic inspection of tires.

A tire inspection method is proposed, comprising a first sequence followed by a second sequence.

The first sequence consists in rotating the tire about its axis while simultaneously performing at least a first acquisition of at least one at least partial macroscopic image of the inner shape and/or the outer shape of the tire, and either comparing the acquired macroscopic image with at least one stored reference image representing a desired toroidal shape of the tire, or analysing this macroscopic image with the aid of digital image processing algorithms, for the purpose of detecting any deviations from the tire standard and delivering either a rejection signal or an acceptance signal for the tire.

The second sequence consists in either discharging the tire if the rejection signal is sent or, if the acceptance signal is sent, rotating the tire about its axis while simultaneously performing at least a second acquisition of at least one at least partial microscopic image of the inner shape and/or the outer shape of the tire, and either comparing the acquired microscopic image with at least one stored reference image representing a desired surface condition of the tire or analysing this microscopic image with the aid of digital image processing algorithms, for the purpose of detecting any deviations from the standard and delivering corresponding signals.

The method may comprise an intermediate sequence between said first and second image acquisitions, which consists in rotating the tire about its axis while simultaneously carrying out an operation of brushing at least part of the outer surface of the tire.

A tire inspection line is also proposed, comprising:
a first inspection post for macroscopic inspection, comprising drive means capable of rotating the tire about its axis and associated image acquisition means for acquiring at least one at least partial macroscopic image of the inner shape and/or the outer shape of the tire;
first electronic means for comparing the acquired macroscopic image with at least one stored reference image representing a desired toroidal shape of the tire, in order to detect any deviations from the standard, these means being capable of delivering either a first rejection signal or a first acceptance signal for the tire;
a second inspection post for microscopic inspection, comprising drive means capable of rotating the tire about its axis and associated image acquisition means for acquiring at least one at least partial microscopic image of the inner surface and/or the outer shape of the tire;
second electronic means for either comparing the acquired microscopic image with at least one stored reference image or analysing this microscopic image with the aid of digital image processing algorithms, these means being capable of delivering corresponding signals; and
transfer means for transferring the tire from the first post to a discharge point, if said rejection signal is sent, or, if said acceptance signal is sent, to the second inspection post.

The inspection line may also comprise an intermediate brushing post comprising brushing means for brushing the outer surface of the tire.

According to a variant embodiment, the intermediate brushing post may comprise separating means for axially separating the beads of the tire.

According to a variant embodiment, the intermediate brushing post may comprise drive means for rotating the tire.

The drive means of the first inspection post may advantageously comprise a rotating shaft having a plurality of spokes forming a support plane on which the tire can be placed.

The second inspection post may advantageously comprise a first inspection station comprising first drive means for rotating the tire about its axis and associated first image acquisition means, a second inspection station comprising second drive means for rotating the tire about its axis and associated second image acquisition means, and transfer means for transferring the tire from the first drive means to the second drive means, these transfer means including means for turning the tire over.

The transfer means may comprise a first gripping robot capable of grasping one bead of the tire and a second gripping robot capable of grasping the other bead of the tire, the means for turning the tire over comprising means for clamping the tread of the tire.

The turnover means may comprise means for grasping the tire by bearing on its tread.

BRIEF DESCRIPTION OF THE DRAWINGS

A tire inspection line and its operation will now be described by way of non-limiting examples, illustrated in the drawing, in which.

DETAILED DESCRIPTION OF EMBODIMENTS OF THE INVENTION

The following description refers to a tire P to be inspected which comprises a peripheral tread R, sidewalls F1 and F1 and annular beads B1 and B2 terminating the inner edges of these sidewalls.

Figure 1:
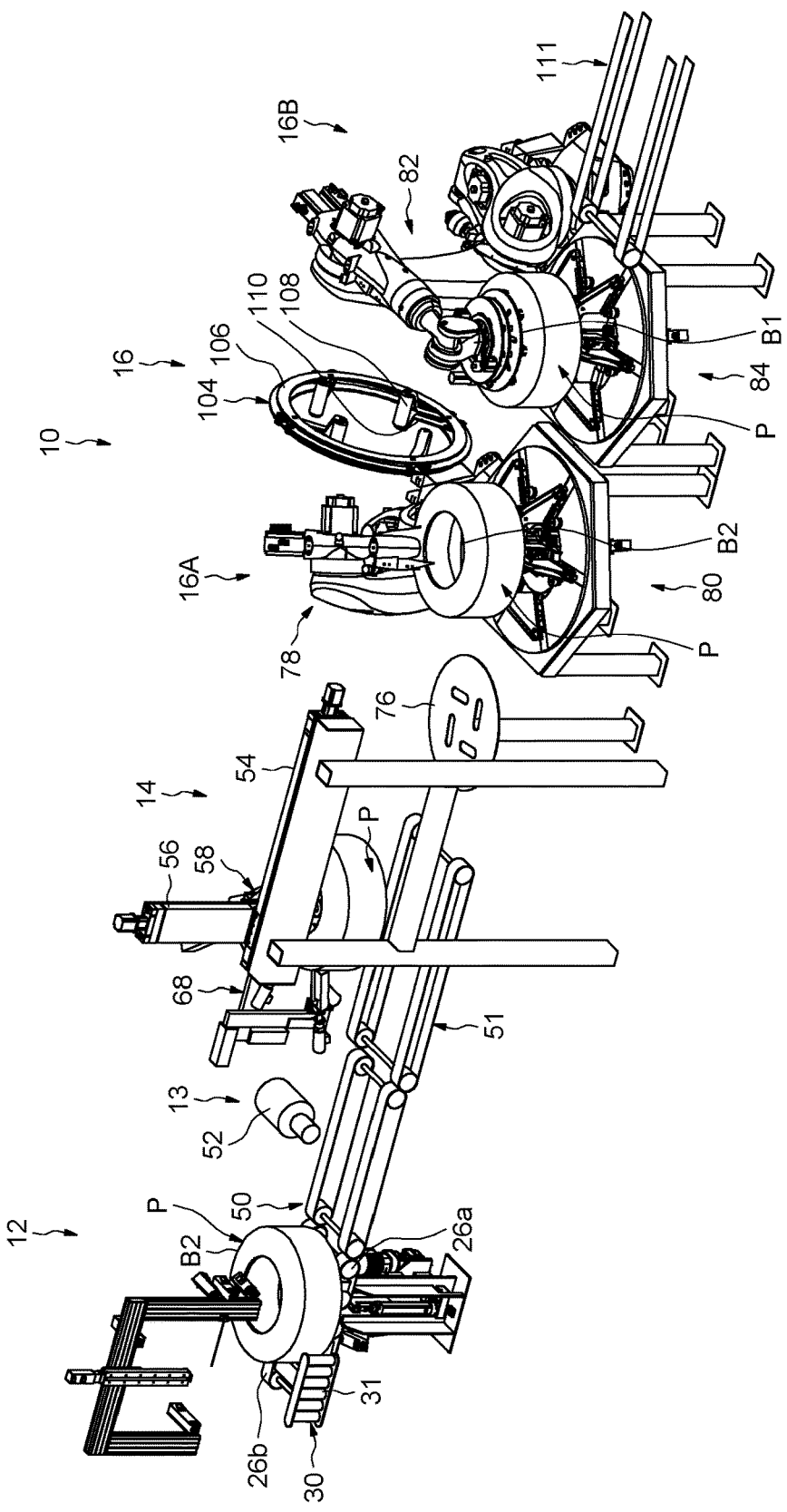
FIG. 1 shows an overall perspective view of an inspection line.

FIG. 1 shows, in a general way, an inspection line 10 for inspecting tires P, comprising, in sequence, a macroscopic inspection post 12 for carrying out a first inspection sequence, a selection post 13, an intermediate brushing post 14 and a microscopic inspection post 16 for carrying out a second inspection sequence if the tires have been accepted at the selection post.

Figure 2:
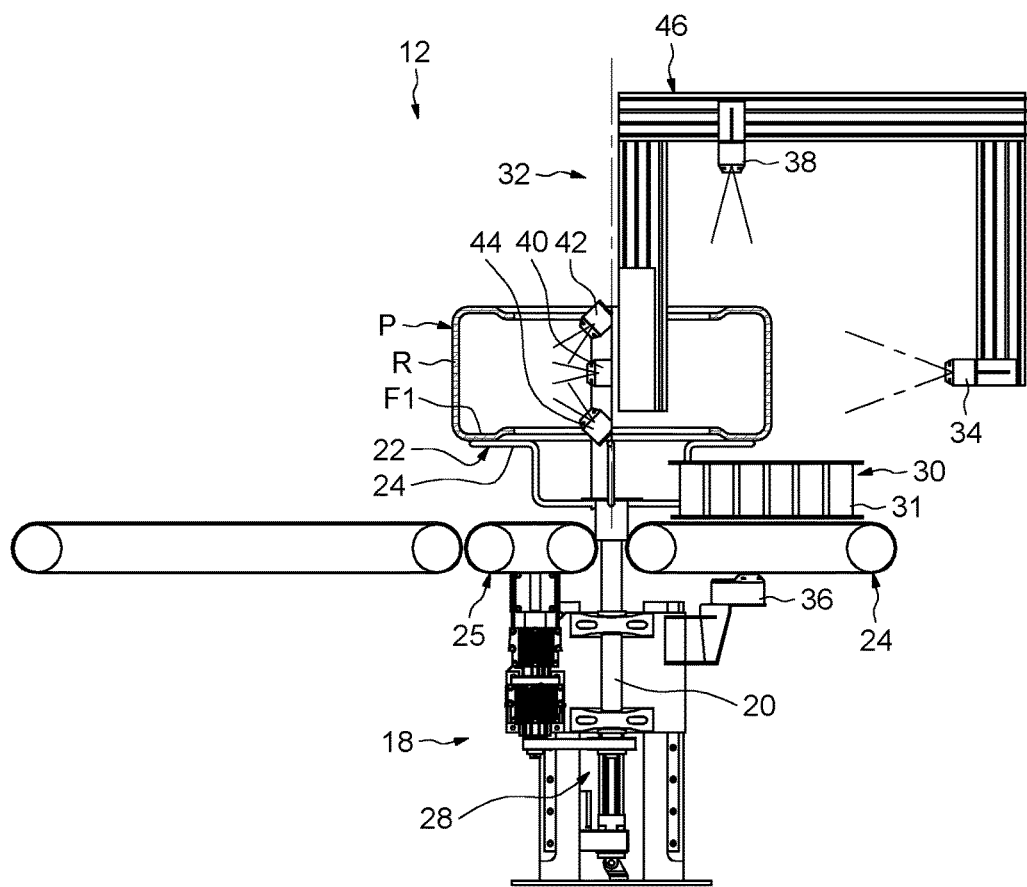
FIG. 2 is a schematic sectional view of a first inspection post of the inspection line for macroscopic inspection.

As shown more particularly in FIGS. 1 and 2, the macroscopic inspection post 12 comprises drive means 18 for rotating a tire P, these means comprising a rotating vertical shaft 20 whose upper end is equipped with a four-arm support 22 composed, for example, of four radial support arms 24 positioned at 90°, which provide a horizontal support plane. These radial arms 24 may, for example, be formed by profiled elements having small circular cross sections.

The macroscopic inspection post 12 comprises horizontal conveying means comprising conveyor belts 24 and 25 composed, respectively of pairs of endless parallel lateral bands 26a and 26b.

The rotating vertical shaft 20 can be moved vertically by a raising mechanism 28, shown schematically, between a lower position, in which the radial support arms 22 are placed below the conveyor belt 24 and 25, and an upper position, in which the radial support arms 22 are placed above the conveyor belts 24.

The tires P arrive at the inspection line lying flat on the conveyor belts 26, for example with the sidewall F1 on the belts, which are activated so as to place the tire P above and at a distance from the four-arm support 22 which is placed in its lower position.

Centring means 30, comprising, for example, rollers 31 with vertical axes, can be used to place the vertical axis of the tire P, preferably, concentrically with the vertical shaft 20, by acting on the tread R of the tire P.

The mechanism 28 is then activated so that the rotating vertical shaft 20 is raised to its aforesaid upper position. When this is done, the four-arm support 22 picks up the tire P by its underside, raises it, and moves it upwards away from the conveyor belts 24 and 25, to place it in an upper inspection position as shown in FIG. 2.

The macroscopic inspection post 12 further comprises image acquisition means 32 for acquiring macroscopic images of the tire P.

These image acquisition means 32 comprise, for example, three external cameras, including a camera 34 orientated so as to view the outer surface of the tread R of the tire P, a camera 36 orientated so as to view the outer surface of the sidewall F1 of the tire P1, and a camera 38 orientated so as to view the outer surface of the sidewall F2 of the tire P.

The image acquisition means 32 comprise, for example, three internal cameras, including a camera 40 orientated so as to view the inner surface of the tread R of the tire P, a camera 42 orientated so as to view the inner surface of the sidewall F1 of the tire P, and a camera 44 orientated so as to view the inner surface of the sidewall F2 of the tire P.

According to a particular embodiment, the external cameras 34 and 36 and the internal cameras 40, 42 and 44 are mounted on a support 46 so that, when the tire P is in its upper inspection position, these cameras are immediately in their desired relative positions with respect to the tire P. On the other hand, the external camera 38 is placed under the conveyor belts 24 and 25, with its field of view passing between the bands 26a and 26b of these belts.

Lighting means (not shown) are also provided for the suitable illumination of the outer and inner surface of the tire P, to ensure that the image acquisition means 32 are effective. These lighting means are arranged to illuminate the areas at which the aforesaid cameras are aimed.

When a tire P is in its aforesaid upper inspection position, the rotating shaft 20 is rotated and causes the rotation of the tire P, this rotation being controlled by an angular indexing sensor C1 (not shown). At the same time, during this rotation, external and internal macroscopic images of the tire P can be acquired by the image acquisition means 32, over one revolution of the tire P for example.

Figure 6:
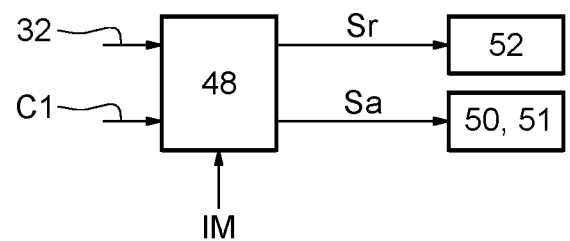
FIG. 6 shows an electronic diagram of an electronic device associated with the first inspection post.

As shown in FIG. 6, the macroscopic inspection post 12 further comprises an electronic device 48 which receives the signals emitted from the image acquisition means 32 and from the corresponding indexing sensors.

The electronic device 48 is programmed so that it produces macroscopic images of the inner and outer surfaces of the tire P, and then either compares the signals representing actual macroscopic images of the tire P with one or more stored reference images IM, or analyses this macroscopic image with the aid of digital image processing algorithms in order to detect any deviations from the standard in respect of the shape of the tire P.

At the end of this comparison, the electronic device 48 delivers either an acceptance signal Sa or a rejection signal Sr.

This comparison consists in comparing the relative spatial positions of spatially separated points or pixels on the outer and/or inner surfaces of the inspected tire P with the stored relative spatial positions of spatially separated points or pixels on the outer and inner surfaces of a reference tire, at a low spatial resolution.

For example, the distance between the points or pixels may be between one and five millimeters. These points or pixels may be defined on spatially separated circumferential generatrices and/or spatially separated generatrices located in planes containing the axis of the tire. It may be noted that the support arms 24 supporting the tire P, which pass in front of the camera 36, do not interfere with the acquisition of the macroscopic image of the outer surface of the tire P, because they are easily identifiable by the electronic device.

When the acquisition carried out by the image acquisition means 32 is completed, the raising mechanism 28 is activated so as to bring the rotating shaft 20 and the four-arm support 22 down into the lower position, while simultaneously repositioning the tire P on the belts 24 and 25.

The belts 24 and 25 are then activated so as to move the tire P on an intermediate belt 50, which is also activated, of the selection post 11.

The macroscopic inspection post 12 is then ready to receive and inspect the next tire P.

When the tire P is fully in place on the intermediate belt 50, this belt is stopped so as to immobilize the tire P at a desired position in the selection post 11.

If the rejection signal Sr is delivered by the electronic device 48, the tire P is removed from the inspection line 10.

The rejection signal Sr activates either an audible or a luminous warning means, and an operator then removes the tire P.

The inspection line 10 may, for example, be equipped with a transverse pusher 52, of the jack type for example, which is activated by the rejection signal Sr and removes the tire P via one side of the intermediate belt 50.

If the acceptance signal Sa is delivered by the electronic device 48, the intermediate belt 50 conveys the tire P towards a belt 51 of the brushing post 12. The belt 51 is activated and then stopped, so as to immobilize the tire P at this brushing post 12.

According to a variant embodiment, the electronic device 48 may be equipped with a display screen for displaying the toroidal shape of the tire P and the desired toroidal shape, and deviations from the standard can be evaluated on this screen. In this case, an operator could decide to reject or accept the tire P.

Figure 3:
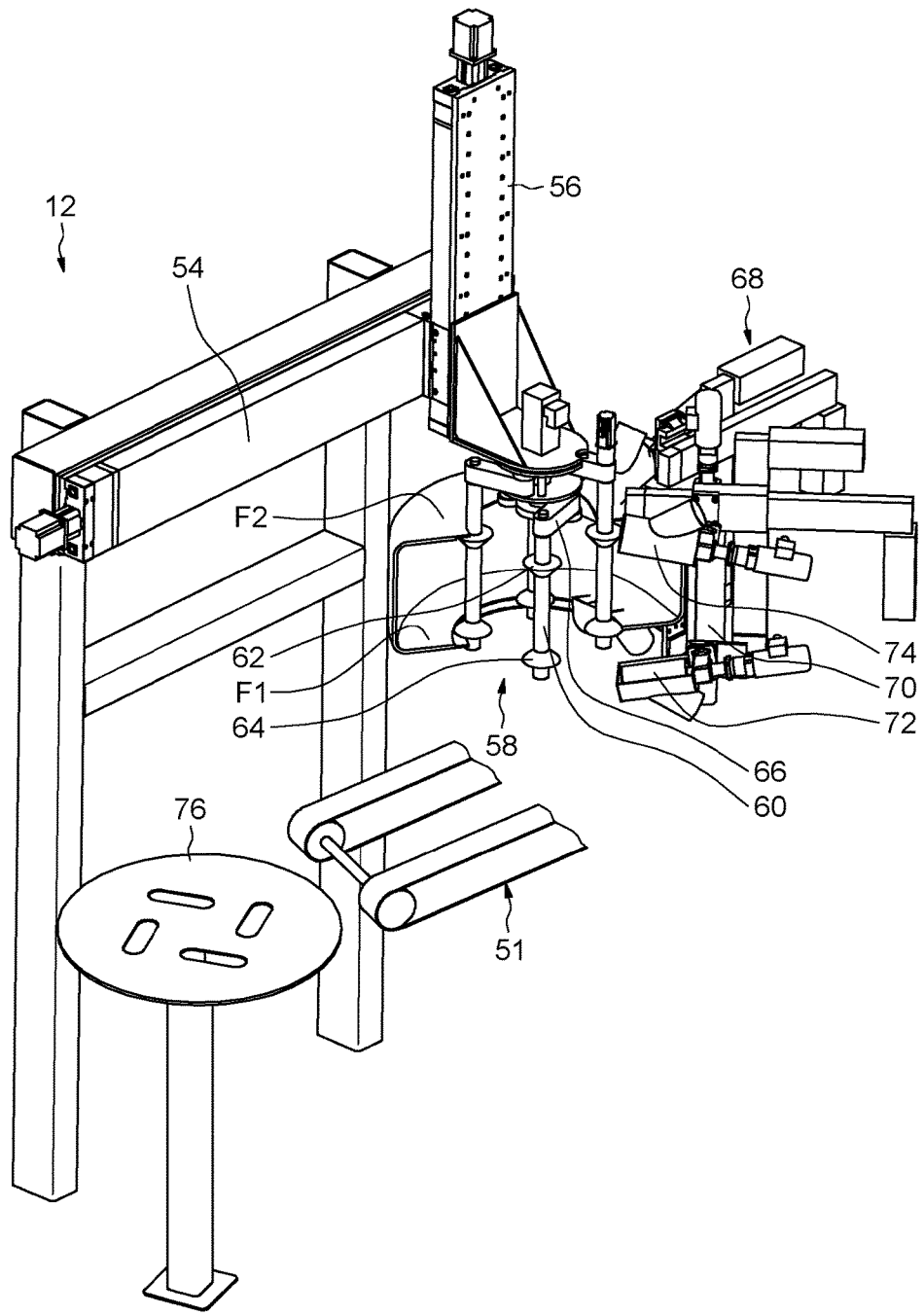
FIG. 3 is a schematic partially sectional perspective view of a brushing post of the inspection line.

As shown schematically in FIGS. 1 and 3, the brushing post 12 comprises a horizontal slide 54 carrying a vertical slide 56 on which is mounted a gripping and rotating device 58 capable of picking up the tire P by its central part and causing it to rotate.

According to an illustrated exemplary embodiment, the gripping and rotating device 58 comprises four vertical pins 60 equipped with pairs of upper and lower supports 62 and 64 spaced apart vertically and projecting laterally, carried by articulated arms 66 which can be driven by means which are not shown.

When a tire P, whose toroidal shape has previously been accepted, arrives at the brushing post 12, the gripping and rotating device 58 is moved downwards along the vertical slide 56 so that the pins 60 penetrate into the axial passage of the tire P. The arms 66 are then driven so as to separate the pins 60 radially as far as the beads B1 and B2 of the tire P, so that the pairs of supports 62 and 64 are between these beads B1 and B2.

The gripping and rotating device 58 is then moved upwards along the vertical slide 56 so that the upper supports 62 pick up and raise the tire P to an upper brushing position visible in FIG. 2.

The upper and lower supports 62 and 64 are then separated by means which are not shown, so as to separate the beads of the tire P in order to make the sidewalls F1 and F2 of the tire as flat as possible.

The brushing post 12 comprises a brushing system 68 including, for example, three brushes 70, 72 and 74, for example cylindrical brushes, the system being capable of moving these brushes, by means of arms or slides and actuators for example, and causing the brushes to rotate by means of motors.

When the tire P is in the aforementioned brushing position, the brushing system 68 is activated to move the brushes 70, 72 and 74 and bring them into contact with the outer surface of the tire P, the brush 70 being in contact with the tread R, the brush 72 being in contact with the sidewall F1, and the brush 74 being in contact with the sidewall F2.

As a result of the combination of the rotation of the tire P about its axis by the device 58 and the rotation of the brushes 70, 72 and 74 by their motors, the outer surface of the tire P is cleaned. In particular, the more or less coarse particles of material which result from the manufacture of the tire P, notably during its removal from the mould, and which are deposited on and adhere to the outer surface of the tire P, are removed.

When the brushing operation is completed, the rotation of the tire P is stopped, and the brushing system 68 is activated so as to separate the brushes 70, 72 and 74 from the tire P.

The vertical slide 56 is then moved along the horizontal slide 54 so as to bring the tire P above a transfer plate 76 and the gripping and rotating device 58 is moved downwards along the vertical slide 56 so as to lay the tire P flat on the transfer plate 76, with its sidewall F1 on this plate 76.

The gripping and rotating device 58 is then moved to execute a cleaning operation on the next tire P.

Figure 4:
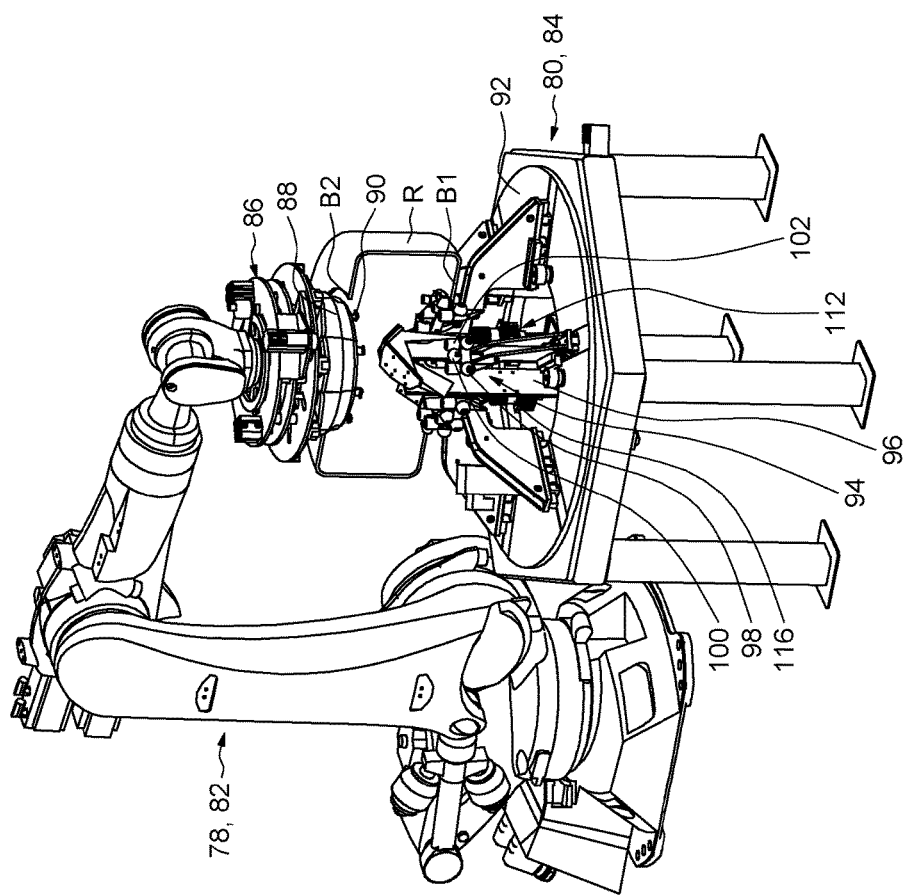
FIG. 4 is a schematic partially sectional perspective view of a second inspection post of the inspection line for microscopic inspection.

As shown in FIGS. 1 and 4, the microscopic inspection post 16 comprises a first microscopic inspection station 16A equipped with a first manipulator robot 78 and a first table 80, and a second microscopic inspection station 16B equipped with a second manipulation robot 82 and a second table 84.

The manipulator robots 78 and 82 comprise, respectively, a gripping and rotating head 86 comprising a rotating centring collar 88 fitted with hooks 90 adapted to grip a bead of a tire P, and comprising a motor (not visible in the figures) adapted to rotate the collar 88.

The tables 80 and 84 comprise a plate 92 and guide modules 94 carried, respectively, by carriages 96 mounted in a radially slidable way relative to a vertical axis on the plate 92. Each module 94 comprises vertically spaced rollers 98 and 100, defining radially outwardly open spaces between them, and centring rollers 102.

When a bead of a tire P is placed peripherally outside the spaces between the rollers 98 and 100 of the modules 94, the actuation of the carriages 96 so that they move radially outward enables the rollers 98 and 100 to be placed on either side of this bead, and enables the centring rollers 102 to be placed against the inner edge of the bead, so that the bead is gripped at different points on its periphery.

Between the microscopic inspection stations 16A and 16B, the microscopic inspection post 16 comprises an inverting or turnover device 104 which comprises, mounted on a support which is not shown, a ring 106, having a horizontal axis for example, equipped with retaining members 108 placed inside the ring and carried by intermediate manoeuvring levers 110, these levers being connected to actuating means (not shown) for moving the retaining members 108 substantially radially relative to the ring 106.

When a brushed tire P is laid flat on the transfer plate 76, the robot 78 of the first microscopic inspection station 16A is activated so that its gripping and rotating head 86 grasps the upper bead B2 of this tire P as described above.

The robot 78 is then activated so as to bring the tire P, held flat, above the table 80 in a position such that the modules 94 of this table 80 can be moved radially outwards and grasp the lower bead B1 of the tire P as described above.

The tire P is then in a first microscopic inspection position in which it can be rotated about its axis by the collar 88 connected to a motor incorporated in the gripping and rotating head 86, its lower bead B2 being guided by the guide modules 94.

Subsequently, when the tire has been immobilized, the modules 94 of the table 80 are moved radially inwards so as to release the lower bead B1 of the tire P as described above.

The robot 78 is then activated in such a way that it removes the tire P from the first inspection station 16A, causes it to pivot in order to place its axis horizontally, and places it across the inner space formed by the retaining members 108 of the inverting device 104, by approaching from one side of the ring 106. The retaining members 108 are then moved so as to bear on the tread R of the tire P at different points on its periphery and thus clamp and retain the tire P.

The gripping and rotating head 86 of the robot 78 then releases the tire P, and the robot 78 is then available to grasp the next tire placed on the transfer plate 76.

After this, the robot 82 of the second microscopic inspection station 16B is activated so that its gripping and rotating head 86, operating as described previously but approaching from the other side of the ring 106, grasps the bead B1, opposite the bead B2 which was gripped by the robot 78, of the tire P retained by the inverting device 104.

The retaining members 108 of the inverting device 104 are then moved to release the tire P.

The robot 82 is then activated so as to bring the tire P, held flat, above the table 84, and the modules 94 of this table 84 are moved so as to grasp the bead B1, which has become the lower bead, of the tire P, as described above.

The tire P is then in a second microscopic inspection position in which it can be rotated by the collar of the gripping and rotating head 86 of the robot 82, its bead B2, which has become the lower bead, being guided by the guide modules 94 of the table 84.

The modules 94 of the table 84 are then moved so as to release the lower bead B2 of the tire P as described above.

The robot 82 is then activated so as to remove the tire P from the second inspection station 16B and place it on a final discharge belt 111, and then to release it by activating the gripping and rotating head 86 of the robot 82.

The robot 82 is then available to grasp the next tire P placed in the inverting device 104.

Figure 5:
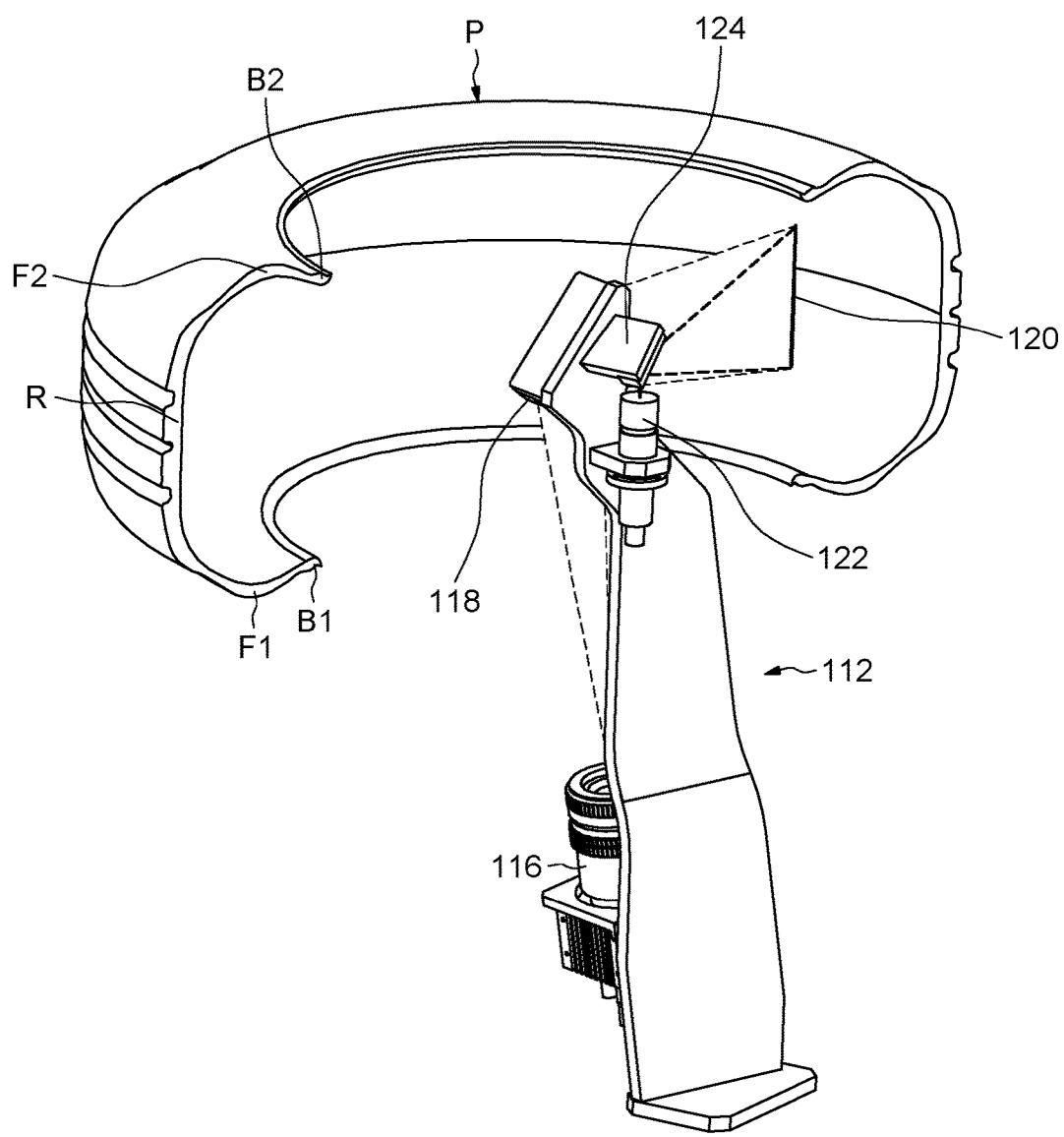
FIG. 5 is a schematic partially sectional perspective view of a detail of the second inspection post of the inspection line for microscopic inspection.

As shown in FIGS. 4 and 5, the microscopic inspection stations 16A and 16B also comprise, respectively, image acquisition means 112, mounted on the tables 80 and 84, for acquiring microscopic images of the inner and outer surfaces of the tire P, and more particularly of the lower half, or slightly more than this, of the tire P which is placed in these inspection stations in the inspection position described above and made to rotate.

For example, each image acquisition means 112 is intended to acquire images of annular surfaces which, when concatenated, cover at least half of the inner and outer surface of the tire P.

As shown in greater detail in FIG. 5, an image acquisition means 112 comprises, for example, the following items mounted on supports 114: cameras 116, mirrors 118 which deflect the fields of view of the cameras 116 towards inspection areas of restricted width 120 on the inner surface of the tire, lighting means 122, and mirrors 124 deflecting the emitted light towards these inspection areas 120, these inspection areas extending perpendicularly to the circumferential direction of the tire.

Some of the image acquisition means 112 may comprise mirrors to be positioned inside the tire P. In this case, movement means are provided to move their supports 114 on the tables 80 and 84 between a central retracted position and an advanced position, so that, when the supports are in the central retracted position, the tire P can be moved vertically to its aforesaid microscopic inspection position and to be removed therefrom as described above.

In an equivalent way, the image acquisition means 112 comprise cameras, associated lighting means and associated mirrors for acquiring images of inspection areas on the lower half of the outer face of the tire P.

When a tire P is in its aforesaid microscopic inspection position, in the microscopic inspection stations 16A and 16B respectively, the tire P is rotated as described previously, this rotation being controlled by an angular indexing sensor C2 and C3 respectively (not shown). During this rotation, external and internal microscopic images of the corresponding half of the tire P can be acquired by the image acquisition means 112, over one revolution of the tire P for example.

Figure 7:
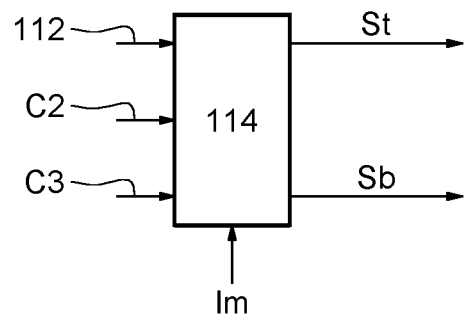
FIG. 7 shows an electronic diagram of an electronic device associated with the second inspection post.

As shown in FIG. 7, the microscopic inspection post 16 further comprises an electronic device 114 which receives the signals emitted from the image acquisition means 112 and from the corresponding indexing sensors C2 and C3.

The electronic device 114 is programmed so that it produces microscopic images of the surface conditions of the inner and outer surfaces of the tire P, and then either compares the signals representing actual microscopic images of the tire P with one or more stored reference images Im representing a desired surface condition of the tire, or analyses these microscopic images with the aid of digital image processing algorithms so as to detect any deviations from the standard and in order to deliver corresponding signals. The electronic device 114 may also be equipped with a display screen (not shown) for displaying the detected deviations. In this case, an operator could decide whether or not to validate the detected deviation, and consequently accept or not accept the tire P.

According to a variant embodiment, the microscopic inspection post 16 could comprise a single microscopic inspection station, equipped with means for acquiring images of the surface conditions of the inner and outer surfaces of the tire P.

The inspection line 10 may be subordinated to an overall electronic control system, so that the tires P can be inspected sequentially in an automatic or partially automatic way.

The various parts of the inspection line 10 described above have the necessary adjustment means for receiving and inspecting tires of different sizes, the electronic devices being programmed accordingly.

The invention claimed is:

1. An inspection method for a tire, the method comprising:
   (A) in a first sequence:
      (1) at a first inspection post of an inspection line for tires, simultaneously utilizing a first rotation driver to rotate the tire about an axis of the tire while utilizing a first image acquisition apparatus to carry out a first acquisition of at least one partial or whole macroscopic image of: an inner shape of the tire, or an outer shape of the tire, or both an inner shape and an outer shape of the tire,
      (2) utilizing a first electronic processor to detect whether a deviation is present by: comparing the at least one macroscopic image with a stored representative reference image, wherein the comparing comprises comparing (i) relative spatial positions of spatially separated pixels of the at least one macroscopic image, the pixels being defined on spatially separated circumferential generatrices and/or spatially separated generatrices located in planes containing an axis of the tire, with (ii) relative spatial positions of spatially separated pixels of the stored representative reference image, and
      (3) utilizing the first electronic processor to output a signal for the tire in accordance with the detection of whether a deviation is present, wherein the signal is a rejection signal, in accordance with a deviation having been detected, and wherein the signal is an acceptance signal, in accordance with a deviation having not been detected; and (B) in a second sequence:
  (1) in accordance with the rejection signal having been output in the first sequence: utilizing a transfer apparatus to transfer the tire from the first inspection post to a discharge point of the inspection line, and discharging the tire, and,
  (2) in accordance with the acceptance signal having been output in the first sequence:
    (a) utilizing the transfer apparatus to transfer the tire from the first inspection post to a second inspection post of the inspection line,
    (b) at the second inspection post, simultaneously utilizing a second rotation driver to rotate the tire about the axis of the tire while utilizing a second image acquisition apparatus to carry out a second acquisition of at least one partial or whole microscopic image of: an inner surface of the tire, or an outer surface of the tire, or both an inner surface and an outer surface of the tire,
    (c) utilizing a second electronic processor to detect whether a local deviation in a surface of the tire is present by: analyzing the at least one microscopic image using digital image processing algorithms, or comparing the at least one microscopic image with a stored reference image representing a desired surface condition of the tire, or both analyzing the at least one microscopic image using digital image processing algorithms and comparing the at least one microscopic image with the stored reference image representing the desired surface condition of the tire, and
    (d) utilizing the second electronic processor to output a signal in accordance with the detection of whether a local deviation is present.

2. The method according to claim 1, the method further comprising, between the first and second sequences, an intermediate sequence at an intermediate brushing post that includes simultaneously utilizing an intermediate rotation driver to rotate the tire about the axis of the tire while utilizing a brush device to carry out an operation of brushing at least part of an outer surface of the tire.

3. An inspection line for tires, comprising:
  (A) a first inspection post arranged to perform macroscopic inspection, the first inspection post including:
    (1) a first rotation driver arranged to rotate a tire about an axis of the tire, and
    (2) a first image acquisition apparatus arranged to acquire at least one partial or whole macroscopic image of one or both of: an inner shape of the tire, and an outer shape of the tire;
    (3) a first electronic processor programmed to (a) detect whether a deviation is present by comparing the at least one partial or whole macroscopic image acquired by the first image acquisition apparatus with at least one stored representative reference image, wherein the comparing comprises comparing (i) relative spatial positions of spatially separated pixels of the at least one macroscopic image, the pixels being defined on spatially separated circumferential generatrices and/or spatially separated generatrices located in planes containing an axis of the tire, with (ii) relative spatial positions of spatially separated pixels of the stored representative reference image, and (b) output a signal for the tire in accordance with the detection of whether a deviation is present, wherein the signal is a rejection signal, in accordance with a deviation having been detected, and wherein the signal is an acceptance signal, in accordance with a deviation having not been detected;

(B) a second inspection post arranged to perform microscopic inspection, the second inspection post including:
    (1) a second rotation driver arranged to rotate the tire about the axis of the tire, and
    (2) a second image acquisition apparatus arranged to acquire at least one partial or whole microscopic image of one or both of: an inner surface of the tire, and an outer surface of the tire;
    (3) a second electronic processor programmed to (a) detect whether a local surface deviation of the tire is present by: analyzing the at least one partial or whole microscopic image using digital image-processing algorithms, or comparing the at least one partial or whole microscopic image with at least one stored reference image representing a desired surface condition of the tire, or both analyzing the at least one partial or whole microscopic image using digital image-processing algorithms and comparing the at least one partial or whole microscopic image with the at least one stored reference image representing a desired surface condition of the tire, and (b) output a detection signal corresponding to a detection result; and
  (C) a transfer apparatus arranged to transfer the tire from the first inspection post to: (1) a discharge point, in accordance with output of the rejection signal by the first electronic processor, and (2) the second inspection post, in accordance with output of the acceptance signal by the first electronic processor.

4. The inspection line according to claim 3, further comprising an intermediate brushing post that includes a brush device arranged to brush the outer surface of the tire.

5. The inspection line according to claim 4, wherein the intermediate brushing post includes a separator arranged to axially separate beads of the tire.

6. The inspection line according to claim 4, wherein the intermediate brushing post includes a rotation driver arranged to rotate the tire.

7. The inspection line according to claim 3, wherein the first rotation driver includes a rotation shaft having a plurality of spokes that form a support plane on which the tire can be placed.

8. The inspection line according to claim 3, wherein the second inspection post further includes: a first inspection station including:
  a second third rotation driver arranged to rotate the tire about the axis of the tire;
  a third image acquisition apparatus; and
  a transfer device structured to transfer the tire from a first inspection station that includes the first rotation driver to a second inspection station that includes the second driver, the transfer device including a turnover device structured to turn the tire over.

9. The inspection line according to claim 8, wherein the transfer device includes:
  a first gripping robot configured to grasp a first bead of the tire; and
  a second gripping robot configured to grasp a second bead of the tire,
  wherein the turnover device includes a clamp configured to clamp a tread portion of the tire.

10. The inspection line according to claim 8, wherein the turnover device includes retainer members for retaining the tire by bearing on a tread portion of the tire.

\* \* \* \* \*